United States Patent [19]

Sellers et al.

[11] Patent Number: 5,282,746
[45] Date of Patent: Feb. 1, 1994

[54] METHOD OF INSTALLING A DENTAL PROSTHESIS

[75] Inventors: Grady C. Sellers, 1330 Church St., Sulphur Springs, Tex. 75482; Jeffrey C. Neilson, Paris, Tex.

[73] Assignee: Grady C. Sellers, Sulphur Springs, Tex.

[21] Appl. No.: 972,140

[22] Filed: Nov. 4, 1992

[51] Int. Cl.$^5$ .................. A61C 13/12; A61C 13/225; A61C 8/00
[52] U.S. Cl. ................................ 433/172; 433/173
[58] Field of Search ............... 433/172, 173, 174, 175, 433/176

[56] References Cited

U.S. PATENT DOCUMENTS

| | | | |
|---|---|---|---|
| 5,152,687 | 10/1992 | Amino | 433/173 |
| 5,169,308 | 12/1992 | Kvist | 433/173 |
| 5,180,303 | 1/1993 | Hornburg et al. | 433/173 |

Primary Examiner—Paul J. Hirsch
Assistant Examiner—Nicholas D. Lucchesi
Attorney, Agent, or Firm—James E. Bradley

[57] ABSTRACT

A method for installing dentures using an implant and an abutment employs a sealing material. The implant has a threaded bore which receives the abutment at a later date. The abutment has a threaded shank and a downward facing shoulder that engages the rim of the implant. Prior to installation, a technician will place a measured amount of bone wax on the abutment shoulder. In another method, the technician places an excess amount of wax and heats the abutment to cause the wax to melt. The technician then screws the abutment into an analog to mold the contour of the wax. The technician then reheats the abutment to cause the wax to reform according to surface tension. The dentist secures the abutment into the implant in a conventional manner.

6 Claims, 2 Drawing Sheets

METHOD OF INSTALLING A DENTAL PROSTHESIS

BACKGROUND OF THE INVENTION

1. Field of the Invention

This invention relates in general to methods of installing a dental prosthesis, and in particular to a method of sealing an abutment to a previously installed implant.

2. Description of the Prior Art

A technique for installing dentures utilizes implants which are implanted into the bone. Tissue is allowed to heal and cover the implant. Once healed, a hole is formed in the tissue and an abutment is attached to the implant. A framework removably attaches to the abutments. The framework is typically a cast member which supports the dentures.

The implants are of several different types. Each implant has a threaded bore which is encircled by a rim. Later when the abutment is to be attached to the implant, the dentist will remove a portion of the tissue for inserting the abutment, then clean the area, then secure the abutment. The abutment has a sealing shoulder and a threaded shank. The threaded shank engages the threaded bore of the implant. The shoulder on the abutment will engage the rim to provide a seal.

One problem that sometimes occurs is that some fluids may be trapped in the threaded bore even after cleaning. Microorganisms in this fluid may leak out and infect the healthy tissue surrounding the abutment and implant.

To avoid this occurrence, dentists try to clean the areas as best as possible. Antibiotic ointments have been used. Also, a glue such as methylmethacrylate has been employed to seal the junction between the abutment and the implant.

SUMMARY OF THE INVENTION

In this invention, bone wax, which is a surgical, inert beeswax, is employed as a sealing agent. In one method, a precise, measured amount of wax is coated on the shoulder area of the abutment. The amount is less than an amount that would result in excess wax extruding from the connection joint when the abutment is screwed into the implant.

In the another method, the shoulder area of the abutment is initially coated with an excess layer of the bone wax. The abutment is then heated to melt the wax. After cooling, a technician will screw the abutment into an analog. An analog as used herein, is a forming or molding member which has the same shape and size of conical bore and rim as the implant which has been previously or is to be installed. The analog is not installed as in implant in a patient. The analog serves as a mold to form and mold the wax into the configuration of the rim of the actual implant. Excess wax will be extruded out and removed.

The technician then unscrews the abutment from the analog. He heats the abutment again to cause the wax to flow slightly according to surface tension. The abutment will now be prepared for securing to an installed implant.

In both cases, the dentist will install the prepared abutment in the same manner as in the prior art. He will secure it by rotating the threaded shank into the threaded bore of the implant. The bone wax will seal the area of the shoulder and rim. If any fluid is trapped in the threaded bore, it will be prevented from leaking out into the vicinity of the healthy tissue.

DETAILED DESCRIPTION OF THE INVENTION

Figure 3:
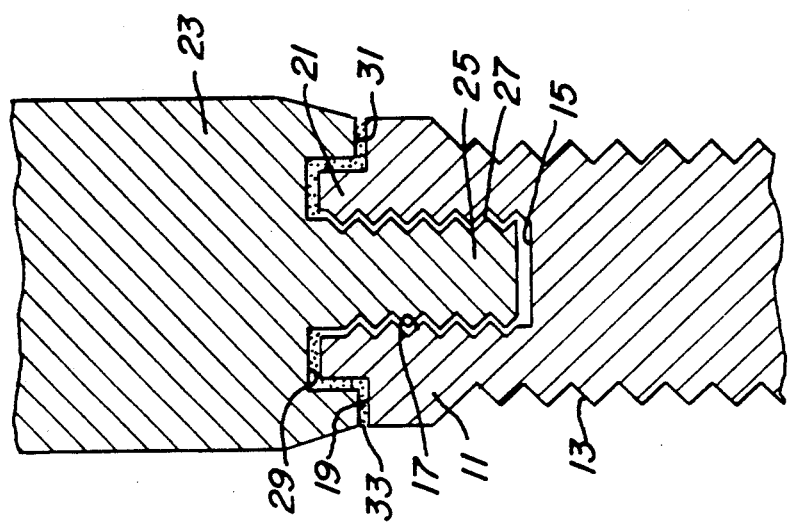
FIG. 3 is a vertical sectional view of the implant and abutment of FIG. 1, shown in a position substantially secured together.
Figure 1:
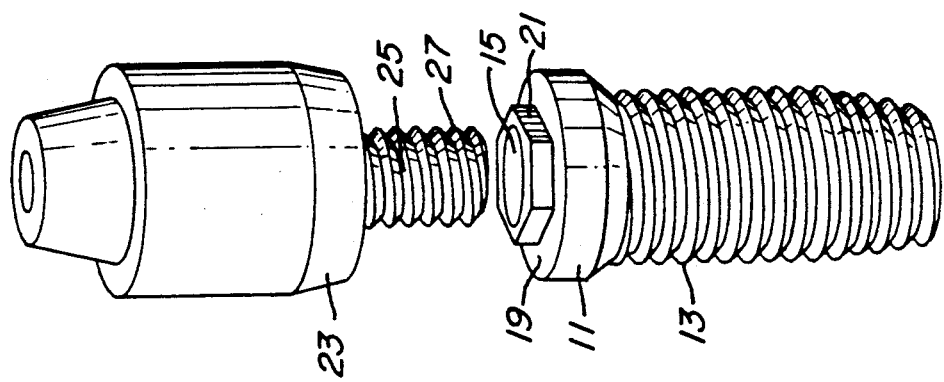
FIG. 1 is a perspective, exploded view showing an implant and abutment for use with the method of this invention.

Referring to FIG. 1, implant 11 is of a conventional type, having external threads 13 which will secure into a threaded hole formed in the bone of a patient. A bore 15 extends part way into implant 11. Bore 15 has internal threads 17, as shown in FIG. 3. A rim 19 encircles bore 15. Rim 19 is in a plane perpendicular to the axis of bore 15 and faces upward. A nut 21 is integrally formed on rim 19 and protrudes upward from rim 19. Nut 21 is a polygonal drive surface for use in screwing the implant 11 into the threaded hole in the bone of the patient. A wrench (not shown) will engage the polygonal drive surfaces of the nut 21.

Figure 2:
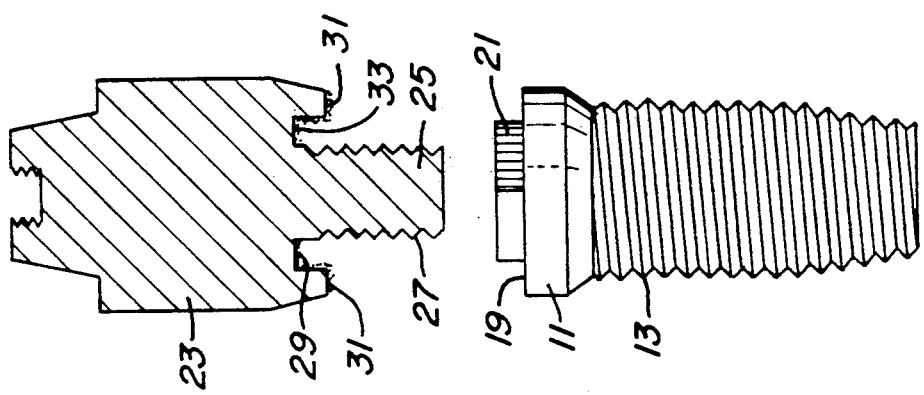
FIG. 2 is a partial sectional exploded view of the implant and abutment of FIG. 1, showing bone wax installed on the abutment.

Abutment 23 is also of a commercially available type. Abutment 23 has a depending shank 25 which has external threads 27. External threads 27 will engage internal threads 17 of implant 11. As shown in FIGS. 2 and 3, an annular recess 29 encircles the upper portion of shank 25. Recess 29 provides a cavity for accommodating nut 21. A shoulder 31 extends downward from recess 29 for engaging rim 19. Shoulder 31 is annular, encircles recess 29, and is located in a plane perpendicular to the axis of shank 25. Abutment 23 is configured for receiving a cast framework containing the dentures (not shown).

In the method of this invention, the implant 11 will be installed in a conventional manner in the patient. External threads 13 will engage a threaded socket formed in the bone of the patient. Healthy tissue will grow over the implant 11.

After a few months, the dentist will provide an opening through the tissue to expose the threaded bore 15. The dentist will clean this area as best as possible. The abutment 23 will have been previously prepared in a special manner. Preferably, the manufacturer has prepared abutment 23 and sent it to the dentist in the prepared form.

This preparation entails applying to portions of abutment 23 a layer of bone wax, which is a beeswax used by orthopedic surgeons. Orthopedic surgeons employ bone wax to fill holes in bones. Bone wax is commercially available and is inert. The wax is indicated by the numeral 33 and the dots shown in FIG. 2. The wax will be filled into the recess 29 and also coated on shoulder 31.

In one method, the amount of wax 33 to be coated has been previously measured precisely. This amount is slightly less or no more than an amount that would result in the wax 33 extruding out of the connection joint between the implant and abutment 23 when screwed together.

In another method, an excess layer of the wax 33 is placed in recess 29 and on shoulder 31. The abutment 23 is then heated to cause the wax 33 to melt and fill recess 29. After the wax has cooled, the technician will then screw the abutment 23 into an analog (not shown) in the laboratory. The analog will likely be an implant 11 that is being used as a mold. The analog must have the same size and shape of bore 15, nut 21 and rim 19. When the technician screws the abutment 23 into the analog, the wax 33 will deform as it contacts the nut 21 and shoulder 31. Excess wax will be extruded out the rim 19 and removed.

The technician then unscrews the abutment 23 from the analog. The technician then heats the abutment 23 to cause the wax 33 to flow. The wax 33 will flow slightly according to surface tension to reform smoothly. The amount of wax 33 will be the precise amount to seal between shoulder 31 and rim 19 without any extrusion out of the connection joint.

Preferably the abutment 23 as prepared will be shipped to the dentist who will be installing the prosthesis. The dentist will install the abutment 23 in the same manner as in the prior art. The dentist will secure the shank 25 in the bore 15 by rotating it in a conventional manner. The wax 33 will form a layer between the shoulder 31 and rim 19. This will seal any trapped fluid in bore 15, preventing it from egressing into the area of the healthy tissue of the patient. FIG. 3 shows an installed condition, but with a gap between shoulder 31 and rim 19 exaggerated to show the location of the wax 33.

Figure 4:
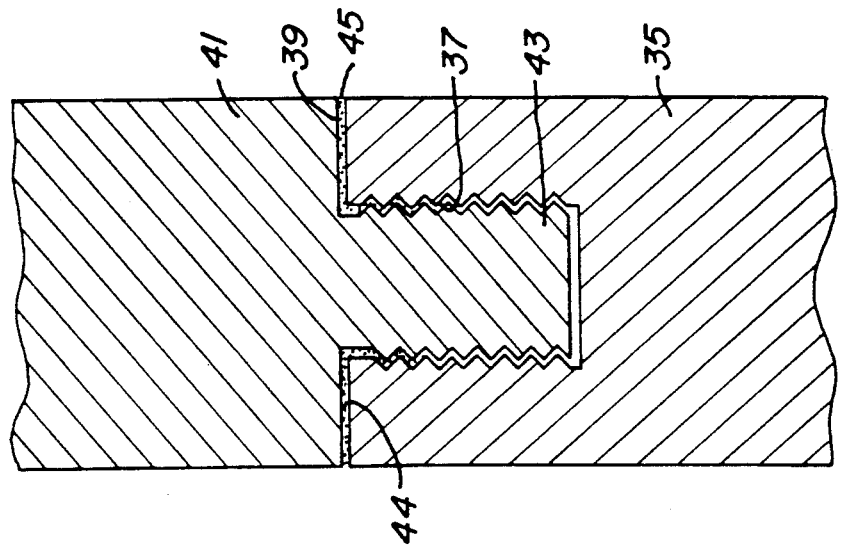
FIG. 4 is a sectional view of second type of abutment and implant for use with the method of this invention.

Referring to FIG. 4, the same method will be employed as previously described. FIG. 4 shows a different type of implant 35. Implant 35 has a rough granular plasma spray coating on the exterior rather than threads 13 of FIG. 1. The rough exterior enhances bone growth to secure the implant 35 in place. Implant 35 has a threaded bore 37 and an upward facing rim 39. Rim 39 in this case extends from bore 37 to the exterior of implant 35.

Abutment 41 has a threaded shank 43 and a downward facing shoulder 44. A precise amount of wax 45 will be coated on shoulder 44 by one of the methods previously described. The dentist installs the abutment 41 in the same manner as previously described. Wax 45 will seal between rim 39 and shoulder 44.

Figure 5:
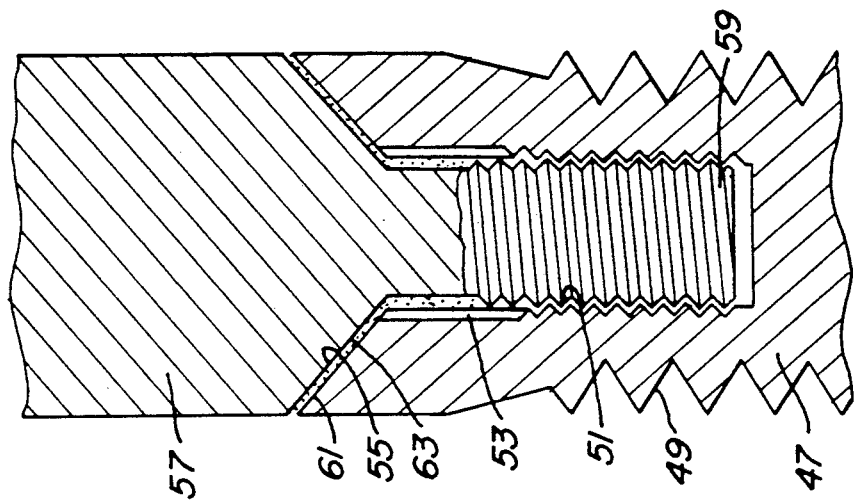
FIG. 5 is a sectional view of a third type of abutment and implant for use with the method of this invention.

In the embodiment of FIG. 5, the same method is employed, however implant 47 is of a different type. Implant 47 has threads 49 on its exterior for engaging a threaded hole in the bone, as in the embodiment of FIGS. 1-3. Implant 47 has an internal threaded bore 51. Drive splines 53 are located in an upper portion of bore 51. Drive splines 53 serve the same purpose as the nut 21 of the embodiments of FIGS. 1-3. A rim 55 encircles bore 51. In this embodiment, rim 55 is conical.

Abutment 57 is also of a conventional type. Abutment 57 has a threaded shank 59. A conical shoulder 61 encircles shank 59. Wax 63 will be coated on shoulder 61 by one of the methods previously described. Wax 63 seals the mating surfaces between shoulder 61 and rim 55.

Figure 6:
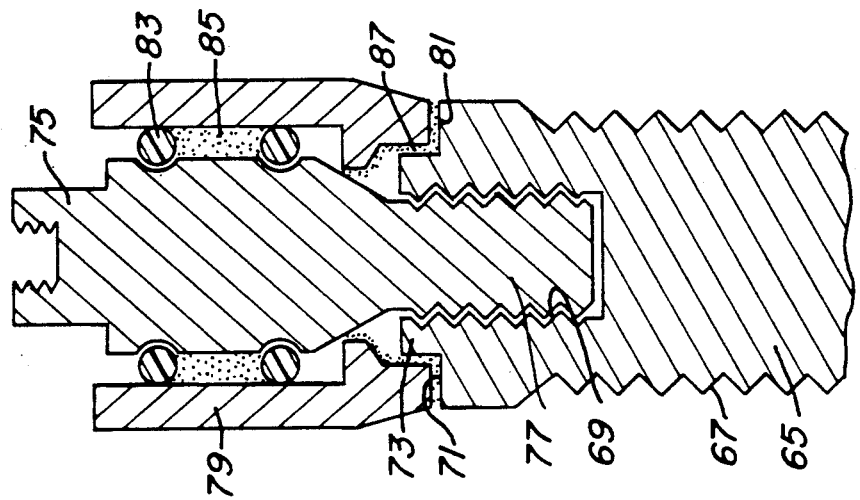
FIG. 6 is a vertical sectional view of a fourth type of abutment and implant for use with the method of this invention.

In the embodiment of FIG. 6, implant 65 has the same configuration as the implant of FIGS. 1-3. It has external threads 67 and a threaded bore 69. Rim 71 encircles bore 69 and faces upward. A nut 73 protrudes upward from rim 71.

Abutment 75 differs from the abutment 23 of FIGS. 1-3, however. Abutment 75 has a threaded shank 77. A sleeve 79 encircles threaded shank 77. Sleeve 79 has a downward facing shoulder 81. O-rings 83 are located between sleeve 79 and abutment 75. In this embodiment, a coating of wax 85 will also be placed between O-rings 83 to further ensure sealing. Wax 87 will be employed on the shoulder 81 in the same manner as previously described.

The invention has significant advantages. The application of bone wax provides better sealing to prevent the egress of any trapped fluids from the implant bore. This reduces the chance for infection.

While the invention has been shown in connection with only four embodiments, it should be apparent to those skilled in the art that it is not so limited but is susceptible to various changes without departing from the scope of the invention.

We claim:

1. A method for installing a dental abutment in a dental implant which has been implanted in bone, the implant having a threaded receptacle with a rim located at an upper end of the receptacle, the abutment having a threaded shank which engages the threaded receptacle and a downward facing shoulder encircling the shank for engaging the rim, the method comprising:
   coating the shoulder with a viscous, flowable, inert material having characteristics of wax; then
   screwing the abutment into the implant, with the material causing the shoulder to seal against the rim to prevent trapped fluids in the receptacle from flowing outward.

2. The method according to claim 1 wherein an amount of the inert material is coated on the shoulder, said amount being selected so as to avoid extrusion of any of the inert material when the abutment is screwed into the implant.

3. A method for installing a dental abutment in a dental implant which has been implanted in bone, the implant having a threaded receptacle with a rim located at an upper end of the receptacle, the abutment having a threaded shank which engages the threaded receptacle and a downward facing shoulder encircling the shank for engaging the rim, the method comprising:
   providing an analog member having a receptacle and a rim with a configuration the same as the receptacle and the rim of the implant which is implanted in the bone;
   coating the shoulder with an inert material having characteristics of wax; then
   after coating the shoulder with the material and prior to screwing the abutment into the implant, first screwing the abutment into the receptacle of the analog member to extrude any excess material; then
   removing the excess material and screwing the abutment into the receptacle of the implant, with the material causing the shoulder to seal against the rim to prevent trapped fluids in the receptacle of the implant from flowing outward.

4. A method for installing a dental abutment in a dental implant which has been implanted in bone, the implant having a threaded receptacle with a rim located at an upper end of the receptacle, the abutment having a threaded shank which engages the threaded receptacle and a downward facing shoulder encircling the shank for engaging the rim, the method comprising:

providing an analog member having a receptacle and a rim with a configuration the same as the receptacle and the rim of the implant which is implanted in the bone;

coating the shoulder with an inert material having characteristics of wax; then after coating the shoulder with the material and prior to screwing the abutment into the implant, first screwing the abutment into the receptacle of the analog member to extrude any excess material; then removing the excess material and heating the abutment to melt the material; then, after the material has cooled, screwing the abutment into the receptacle of the implant, with the material causing the shoulder to seal against the rim to prevent trapped fluids in the receptacle of the implant from flowing outward.

5. A method for installing a dental abutment in a dental implant which has been implanted in bone, the implant having a threaded receptacle with a rim located at an upper end of the receptacle, the abutment having a threaded shank which engages the threaded receptacle and a downward facing shoulder encircling the shank for engaging the rim, the method comprising:

coating the shoulder with wax in an amount that is selected to be no more than an amount that would result in the wax extruding when the abutment is screwed into the implant; then screwing the abutment into the receptacle of the implant, with the wax causing the shoulder to seal against the rim to prevent trapped fluids in the receptacle from flowing outward.

6. A method for installing a dental abutment in a dental implant which has been implanted in bone, the implant having a threaded receptacle with a rim located at an upper end of the receptacle, an upward extending polygonal drive nut protruding from the rim, the abutment having a threaded shank which engages the threaded receptacle and a downward facing shoulder encircling the shank for engaging the rim, the shoulder encircling a counterbore which receives the drive nut, the method comprising:

providing an analog member having a receptacle and a rim with a configuration the same as the receptacle and the rim of the implant which is implanted in the bone;

coating the shoulder and counterbore with wax; then heating the abutment to melt the wax and allowing the wax to cool; then screwing the abutment into the receptacle of the analog member to extrude any excess wax; then removing the abutment from engagement with the analog member, removing the excess wax, and heating the abutment again to reform the wax; then allowing the wax to cool, and screwing the abutment into the receptacle of the implant, with the wax causing the shoulder to seal against the rim of the implant to prevent trapped fluids in the receptacle of the implant from flowing outward.

* * * * *